United States Patent [19]

Karpf et al.

[11] Patent Number: 5,245,056
[45] Date of Patent: Sep. 14, 1993

[54] PRODUCTION OF OXETANONES

[75] Inventors: Martin Karpf, Reinach; Ulrich Zutter, Basel, both of Switzerland

[73] Assignee: Hoffmann-La Roche Inc., Nutley, N.J.

[21] Appl. No.: 653,846

[22] Filed: Feb. 11, 1991

[30] Foreign Application Priority Data

Feb. 23, 1990 [CH] Switzerland .......................... 589/90
Dec. 12, 1990 [CH] Switzerland .......................... 3925/90

[51] Int. Cl.$^5$ .......................................... C07D 305/08
[52] U.S. Cl. ..................................... 549/510; 549/511
[58] Field of Search ..................... 549/513, 510, 511

[56] References Cited

U.S. PATENT DOCUMENTS

| | | | |
|---|---|---|---|
| 3,457,193 | 7/1969 | Tinsley et al. | 549/510 |
| 4,395,561 | 7/1983 | Baum et al. | 549/510 |
| 4,931,463 | 6/1990 | Barbier et al. | 514/422 |
| 4,983,746 | 1/1991 | Barbier et al. | 549/378 |

FOREIGN PATENT DOCUMENTS

WO88/10258 12/1988 European Pat. Off.
2400429 7/1975 Fed. Rep. of Germany.

OTHER PUBLICATIONS

Barbier et al., Helvetica Chimica Acta, 70:1412–1418 (1987).
Barbier et al., Helvetica Chimica Acta, 70:196–202 (1987).
Barbier et al., J. Org. Chem., 53:1218–21 (1988).
Garnero et al., Chem. Abstracts, 110:134946 (Abstr#110:134949) (1989).
Derwent Abstract of WO 88/10258, Dec. 1988.
B. M. Lawrence, Flavors and Fragrances, A World Perspective 1988 Elsevier Science Publishers B. V. Amsterdam.

*Primary Examiner*—C. Warren Ivy
*Assistant Examiner*—Raymond Covington
*Attorney, Agent, or Firm*—George M. Gould; George W. Johnston; William Krovatin

[57] ABSTRACT

The invention relates to a novel process for producing a compound having the formula

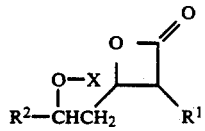

I wherein $R^1$, $R^2$ and X are described herein, via wherein R corresponding β-keto- and β-hydroxy-δ-lactones, as well as novel intermediates which occur in the process.

9 Claims, No Drawings

PRODUCTION OF OXETANONES

BACKGROUND OF THE INVENTION

Field of the Invention

The invention relates to the production of oxetanones and intermediates formed in the production of oxetanones.

SUMMARY OF THE INVENTION

The present invention is concerned with a novel process for producing compounds having the formula.

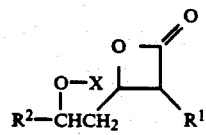   I wherein $R^1$ and $R^2$ each are independently alkyl with up to 17 C atoms optionally interrupted by an O atom in a position other than the α- or β-position; or benzyl optionally ring-substituted by 1 or 3 $C_{1-6}$-alkyl or $C_{1-6}$-alkoxy groups, X is hydrogen or a group of the formula $(R^3, R^4)NCH(R^5)(CH_2)_n$—CO—, $R^3$ is hydrogen, $C_{1-3}$-alkyl or $C_{1-3}$-alkanoyl, $R^4$ is hydrogen or $C_{1-3}$-alkyl and $R^5$ is hydrogen a group Ar or Ar-$C_{1-3}$-alkyl or $C_{1-7}$-alkyl optionally interrupted by Y and optionally substituted by Z or $R^4$ with $R^5$ form together with the N atom to which they are attached to a 4- or 6-membered saturated ring, Y is oxygen, sulphur or a group $N(R^6)$ $C(O)N(R^6)$ or $N(R^6)C(O)$, Z is a group —(O or S)—$R^7$, —$N(R^7, R^8)$, —$C(O)N(R^7, R^8)$ or —$N(R^7)C(O))R^8$, n is the number 1 or 0, whereby $R^5$ is hydrogen when n is the number 1, Ar is phenyl substituted by 1 to 3 groups $R^9$ or $OR^9$ and $R^6$ to $R^9$ are hydrogen or $C_{1-3}$-alkyl, and of salts of the compounds of formula I in which X is not hydrogen with weak acids.

The process in accordance with the invention comprises the steps of:

a) etherifying a β-hydroxy-δ-lactone of the formula

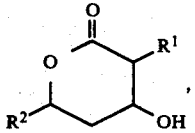   II b) opening the resulting ether of the formula

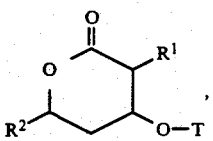   III wherein T is a readily cleavable ether group, with a base, c) reacting the resulting salt of the formula

   IV wherein M is an alkali metal or alkaline earth metal, in optional sequence with an arylmethyl halide and a base and d) selectively cleaving the resulting diether of the formula

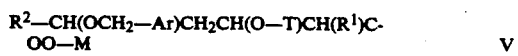   V with an acid, e) cyclizing the resulting B-hydroxyacid of the formula

   VI p0 optionally after resolution into its enantiomers, f) cleaving the resulting B-lactone ether of the formula

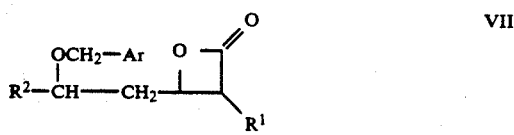   VII and g) if desired, esterifying the resulting β-lactone alcohol of formula I in which X is hydrogen with an agent which introduces the group X and h) if desired, isolating the ester obtained in the form of a salt with a weak acid.

Further, the invention is concerned with novel intermediates which occur in the process.

DETAILED DESCRIPTION OF THE INVENTION

The present invention is concerned with a novel process for the producing compounds having the formula

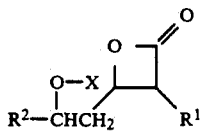   I wherein $R^1$ and $R^2$ each are independently alkyl with up to 17 C atoms optionally interrupted by an O atom in a position other than the α- or β-position; or benzyl optionally ring-substituted by 1 or 3 $C_{1-6}$-alkyl or $C_{1-6}$-alkoxy groups, X is hydrogen or a group of the formula $(R^3, R^4)NCH(R^5)(CH_2)_n$—CO—, $R^3$ is hydrogen, $C_{1-1}$-alkyl or $C_{1-3}$-alkanoyl, $R^4$ is hydrogen or $C_{1-3}$-alkyl and $R^5$ is hydrogen a group Ar or Ar—$C_{1-3}$-alkyl or $C_{1-7}$-alkyl optionally interrupted by Y and optionally substituted by Z or $R^4$ with $R^5$ form together with the N atom to which they are attached to a 4- or 6-membered saturated ring, Y is oxygen, sulphur or a group $N(R^6)$, $C(O)N(R^6)$ or $N(R^6)C(O)_7$, Z is a group —(O or S)—$R^7$, —$N(R^7, R^8)$, —$C(O)N(R^7, R^8)$ or —$N(R^7)C(O))R^8$, n is the number 1 or 0, whereby $R^5$ is hydrogen when n is the number 1, Ar is phenyl substituted by 1 to 3 groups $R^9$ or $OR^9$ and $R^6$ to $R^9$ are hydrogen or $C_{1-3}$-alkyl, and of salts of the compounds of formula I in which X is not hydrogen with weak acids.

Further, the invention is concerned with novel intermediates which occur in the said process.

Compounds of formula I are known, for example, from EP 185 359A2. They possess valuable pharmacological properties. In particular, they inhibit pancreas lipase and can accordingly be used for the control or prevention of illnesses, especially of obesity, hyperlipemia, atherosclerosis and arteriosclerosis.

The process in accordance with the invention comprises the steps of:

a) etherifying a β-hydroxy-δ-lactone of the formula

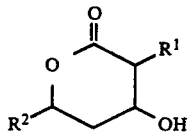

b) opening the resulting ether of the formula

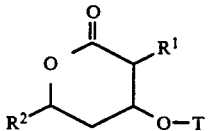

wherein T is a readily cleavable ether group, with a base, c) reacting the resulting salt of the formula

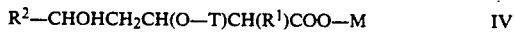

wherein M is an alkali metal or alkaline earth metal, in optional sequence with an arylmethyl halide and a base and d) selectively cleaving the resulting diether of the formula

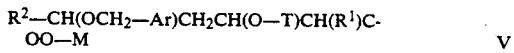

with an acid, e) cyclizing the resulting βhydroxyacid of the formula

optionally after resolution into its enantiomers, f) cleaving the resulting B-lactone ether of the formula

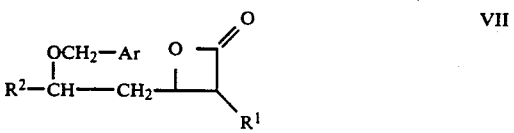

and g) if desired, esterifying the resulting β-lactone alcohol of formula I in which X is hydrogen with an agent which introduces the group X and h) if desired, isolating the ester obtained in the form of a salt with a weak acid.

Alkyl groups are straight-chain or branched hydrocarbon residues and examples include but are not limited to methyl, ethyl, propyl, isopropyl, butyl, isobutyl, pentyl, hexyl, undecyl, hexadecyl and heptadecyl. Phenyl, tolyl and xylyl are examples of aryl groups. Pyrrolidinyl and pyridinyl are examples of 4- to 6-membered saturated rings.

Examples of weak acids which can form salts with the compounds of formula I include but are not limited to p-toluenesulphonic acid, methanesulphonic acid, oxalic acid, ascorbic acid, fumaric acid, maleic acid, malic acid, citric acid and phosphoric acid.

Examples of readily cleavable ether groups include but are not limited to tetrahydro-2H-pyran-2-yl (THP), 1-ethoxyethyl or silyl ether groups such as tri-$C_{1-4}$-alkyl- or mono-(aryl-$C_{1-4}$-alkyl)-di-($C_{1-4}$-alkyl)silyl groups, for example, t-butyldimethylsilyl.

A THP ether of formula III can be prepared by reacting a β-hydroxy-δ-lactone of formula II with 3,4-dihydro-2H-Pyran at about 50° C. in a solvent such as t-butyl methyl ether (TBME), tetrahydrofuran (THF) or toluene in the presence of catalytic amounts of acid such as pyridinium P-toluenesulphonate or p-toluenesulphonic acid. The THP ether III can subsequently be opened using an alkali metal hydroxide, such as sodium hydroxide or potassium hydroxide.

A silyl ether III can be prepared by reacting the β-hydroxy-δ-lactone II with a silyl halide such as t-butyldimethylsilyl chloride in the presence of a base such as ethyldiisopropylamine in a solvent such as dimethylformamide (DMF) while heating, for example, to 50°-100° C. The opening of a silyl ether III can be performed with an alkaline or alkaline earth base such as potassium hydroxide in a solvent such as dioxan.

An alkali metal hydride such as NaH or, preferably, an alkali metal t-butylate conveniently Na t-butylate, can be used as the base in the etherification of the alkali metal or alkaline earth metal salt of formula IV to the diether V. This etherification can be performed by treating the salt IV with for example, benzyl bromide and NaH or Na t-butylate in a solvent such as THF or TBME.

A diether V can be selectively cleaved with an acid such as hydrochloric acid in the case of a THP ether or acetic acid in the case of a silyl ether at a temperature up to about 60° C.

The optional resolution of a racemic β-hydroxyacid VI can be effected using a chiral amine such as (R)-(+)- or (S)-(−)-α-methylbenzylamine in a solvent such as an ester, for example, methyl acetate or ethyl acetate.

A β-hydroxyacid VI can be cyclized with an arylsulphonyl halide such as benzenesulphonyl chloride in a solvent such as pyridine while cooling to about −10° C.

The cleavage of the β-lactone ether VII can be carried out by hydrogenation in a solvent such as a hydrocarbon or halogenated hydrocarbon, for example, hexane or methylene chloride, an ester or ether, for example ethyl acetate or THF over a catalyst such as palladium-on-charcoal (Pd/C) at a temperature up to about 40° C.

The optional esterification of a β-lactone alcohol of formula I in which X is hydrogen with an acid of the formula $(R^3, R^4)NCH(R^5)(CH_2)_n$-COOH can be performed in the presence of triphenylphosphine and of diethyl azodicarboxylate in a solvent such as an ether, for example. THF, at a temperature up to about −15° C.

A β-hydroxyacid of formula VI above can also be prepared by a) esterifying a salt of formula IV above with a halide of the formula $R^{10}$-Hal, wherein R is $C_{1-4}$-alkyl or aryl-$C_{1-4}$-alkyl, and Hal is a halogen, that is, fluorine, chlorine, bromine or iodine, b) etherifying the resulting ester of the formula $$R^2\text{—CHOHCH}_2\text{CH(O—T)COO—}R^{10} \qquad \text{IV-A}$$

and c) in optional sequence saponifying and cleaving in the β-position the resulting diether of the formula $$R^2\text{—CH(OCH}_2\text{—Ar)CH}_2\text{CH(O—T)CH(}R^{1}\text{-)COO—}R^{10} \qquad \text{V-A.}$$

The esterification of a salt IV with a halide $R^{10}$-Hal, for example, with benzyl bromide, can be carried out in a solvent such as THF.

The etherification of the alcohol ester IV-A can be effected with a chloride of the formula Ar-$CH_2OC(NH)CCl_3$, for example, with benzyl 2,2,2-trichloroacetimidate, in the presence of an acid such as trifluoromethanesulphonic acid in a solvent such as cyclohexane, hexane or methylene chloride.

A diether V-A can firstly be treated with an acid such as aqueous acetic acid in the case of a silyl ether or such as hydrochloric acid in the case of a THP ether in a solvent such as dioxan at a temperature up to the reflux temperature of the reaction mixture and subsequently saponified in a solvent such as an alkanol, for example, methanol, using a strong base such as an alkali metal or alkaline earth metal hydroxide, for example, potassium hydroxide, at a temperature up to about 70° C.

It is also possible to prepare a β-hydroxyacid VI by
a) esterifying a β-hydroxy-δ-lactone II,
b) opening the resulting ester of the formula

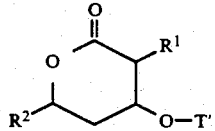
III' wherein T' is aroyl, by acidic catalysis in the presence of an alcohol of the formula to give an ester of the formula $$R^2\text{—CHOHCH}_2\text{CH(O—T')CH(}R^{1}\text{)COO—}R^{10} \qquad \text{IV-B}$$

c) etherifying the ester of formula IV-B and
d) doubly-saponifying the resulting ether diester of the formula $$R^2\text{—CH(OCH}_2\text{—Ar)CH}_2\text{CH(O—T')CH(}R^{1}\text{-)COO—}R^{10} \qquad \text{V-B.}$$

The esterification of the β-hydroxy-δ-lactone of formula II can be carried out for example, with a functional derivative of an acid of the formula Ar—COOH, for example, an acid halide or acid anhydride such as benzoic anhydride, and a strong acid such as perchloric acid or a base such as dimethylaminopyridine as the catalyst in a solvent such as toluene and the subsequent opening of the ester III' can be carried out by acidic catalysis for example, in the presence of an acid such as sulphuric acid or hydrochloric acid with an alcohol of the formula for example, a lower alkanol such as methanol, optionally in a solvent such as toluene, at a temperature up to about 60° C.

The etherification of the alcohol ester IV-B can be performed in analogy to the etherification of the alcohol ester IV-A described above.

The saponification of an ether diester V-B can be carried out in a solvent such as an alkanol, for example, methanol, using a strong base such as an alkali metal or alkaline earth metal hydroxide, for example, potassium hydroxide, at a temperature up to about 70° C.

The β-hydroxy-δ-lactones of formula II can be prepared by
a) saponifying a β-hydroxyester of the formula $$R^2\text{—CHOHCH}_2\text{COO—R} \qquad \text{VIII}$$

wherein R is $C_{1-4}$-alkyl, b) reacting the imidazolide of the resulting β-hydroxyacid of the formula $$R^2\text{—CHOHCH}_2\text{COOH} \qquad \text{IX}$$

with the Mg salt of the malonic acid ester derivative of the formula $$\text{HOCOCH(}R^{1}\text{)COO—R} \qquad \text{X}$$

c) cyclizing the resulting δ-hydroxy-β-ketoester of the formula $$R^2\text{—CHOHCH}_2\text{COCH(}R^{1}\text{)COO—R} \qquad \text{XI}$$

and d) catalytically hydrogenating the resulting β-keto-δ-lactone of the formula

XII

The saponification of the β-hydroxyester of formula VIII can be carried out in a solvent such as dioxan with a base such as sodium hydroxide in a solvent such as methanol.

The magnesium salt of a malonic acid ester derivative of formula X can be prepared by reacting the malonic acid diester of the formula $CH_2(COOR)_2$ with a solution of sodium methylate in methanol and with a halide of the formula $R^{1}$-Hal, for example, the bromide, at a temperature up to the reflux temperature of the solvent. The resulting malonic acid diester derivative of the formula $R^{1}$—CH(COOR)$_2$ is then hydrolyzed with an alkali metal hydroxide, for example, potassium hydroxide, in a lower-alkanol R-OH such as methanol to the monoester of formula X and the latter is converted into the desired magnesium salt with magnesium chloride in THF in the presence of triethylamine at about 0° C.

The imidazolide of the β-hydroxyacid of formula IX can be prepared by reacting this in THF with 1,1'-carbonyldiimidazole.

The magnesium salt of the monoester of formula X can be reacted at room temperature with the imidazolide of the β-hydroxyacid of formula IX to give the δ-hydroxy-β-ketoester of formula XI.

The latter can be cyclized to the β-keto-δ-lactone of formula XII in a solvent such as ethyl acetate with an acid such as hydrochloric acid or a base such as sodium hydroxide.

The catalytic hydrogenation of this lactone to the β-hydroxy-δ-lactone of formula II can be carried out in a solvent such as ethyl acetate or an ether such as THF in the presence of Raney-nickel.

The β-hydroxy-δ-lactones of formula II can also be prepared by a) reacting a β-ketoester of the formula $$CH_3COCH(R^1)COO-R \qquad XIII$$

with an ester of the formula $$R^2-COO-R \qquad XIV$$

b) cyclizing the resulting diketoester of the formula $$R^2-COCH_2COCH(R^1)COO-R \qquad XV$$

and c) catalytically hydrogenating the resulting pyrone of the formula

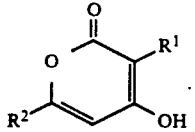

XVI

A β-ketoester of formula XIII can be prepared by alkylating the corresponding β-ketoester of the formula $CH_3COCH_2COOR$ with a halide of the formula $R^1$-Hal, for example, the bromide, in a methanolic sodium methylate solution at a temperature up to the reflux temperature of the reaction mixture.

The reaction of the β-ketoester of formula XIII with an ester of formula XIV can be carried out in the presence of sodium hydride in a solvent such as THF and in the presence of butyllithium in hexane while cooling, for example, at −10° C.

The cyclization to a pyrone of formula XVI can be performed in a solvent such as toluene in the presence of 1,8-diazabicyclo[5.4.0]undec-7-ene(1,5,5) (DBU).

The pyrone of formula XVI can be hydrogenated to the β-hydroxy-δ-lactone of formula II in the same manner as described above for the catalytic hydrogenation of the β-keto-δ-lactone of formula XII.

A β-keto-δ-lactone of formula XII can also be prepared by a) reacting a β-ketoester of the formula $$CH_3COCH(R^1)COO-R \qquad XIII$$

with an aldehyde of the formula $$R^2-CHO \qquad XVIII$$

and b) cyclizing δ-hydroxy-β-ketoester of formula XI.

The reaction of the β-ketoester of formula XIII with the aldehyde of formula XVII can be carried out in the same manner as the reaction with the ester of formula XIV described above.

The cyclization of the δ-hydroxy-β-ketoester of formula XI to the β-keto-δ-lactone of formula XII can be performed with water, conveniently at room temperature (about 20° C).

Further, a β-keto-δ-lactone of formula XII can be prepared by a) etherifying a β-hydroxyester of the formula $$R^2-CHOHCH_2COO-R \qquad VIII,$$

b) saponifying the resulting ether of the formula $$R^2-CH(OCH_2-Ar)CH_2COO-R \qquad XVIII,$$

c) halogenating the resulting ether acid of the formula $$R^2-CH(OCH_2-Ar)CH_2COOH \qquad XIX,$$

d) reacting the resulting acid halide with Meldrum acid, e) hydrogenolyzing the resulting compound of the formula

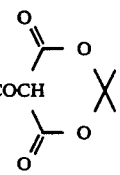

XX and cyclizing to a β-keto-δ-lactone of the formula

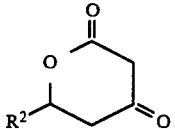

XXI and f) reacting the β-keto-δ-lactone of formula XXI above with an aldehyde which introduces the group $R^1$ or $-CH_2-R^{11}$ and which has the formula $$R^{11}-CHO \qquad XXII$$

wherein $R^{11}$ together with the methylene group represents the group $R^1$, to give a β-keto-δ-lactone of formula XII above.

The etherification of the β-hydroxyester of formula VIII to give the ether of formula XVIII can be carried out in a solvent such as cyclohexane, for example, with benzyl trichloroacetimidate in the presence of trifluoromethanesulphonic acid at a temperature up to about 30° C.

The saponification of the ether of formula XVIII to give the ether acid of formula XIX can be performed with an alkali metal hydroxide such as potassium hydroxide in a solvent such as methanol.

The halogenation of the ether acid of formula XIX can be carried out for example, with oxalyl chloride in a solvent such as methylene chloride at a temperature up to about 25° C.

The reaction of the resulting acid halide with Meldrum's acid can be carried out in a solvent such as methylene chloride in the presence of a base such as pyridine while cooling to about −10° C.

The hydrogenolysis and cyclization of the compound of formula XX to give the β-keto-δ-lactone of formula XXI can be effected in a solvent such as ethyl acetate using a catalyst such as Pd/C.

The reaction of the β-keto-δ-lactone of formula XXI with the aldehyde of the formula R[11]—CHO to give the β-keto-δ-lactone of formula XII is effected for example, with a boran-amine complex such as boranetriethylamine, borane-trimethyl-amine or borane-morpholine in a solvent such as methanol at a temperature up to about 50° C.

A β-keto-δ-lactone of formula XXI can also be prepared by a) reacting the imidazolide of the β-hydroxyacid of the above formula

$$R^2\text{—CHOHCH}_2\text{COOH} \qquad \text{IX}$$

with the Mg salt of a mono-lower alkyl malonate and
b) cyclizing the resulting δ-hydroxy-β-ketoester of the formula

$$R^2\text{—CHOHCH}_2\text{COCH}_2\text{COO—R} \qquad \text{XXIII}$$

to give the β-keto-δ-lactone of formula XXI above.

The preparation of the Mg salt of a mono-lower alkyl malonate, the reaction of this salt with the imidazolide of the β-hydroxyacid of formula IX to give the δ-hydroxy-β-ketoester of formula XXIII and its cyclization to give the β-keto-δ-lactone of formula XXI can be carried out as described above for the preparation of the β-hydroxy-δ-lactone of formula II via the imidazolide of the β-hydroxyacid of formula IX and the Mg salt of the malonic acid ester derivative of formula X.

A preferred embodiment of the process of the present invention comprises reacting a β-ketoester XIII with an aldehyde XVII, cyclizing the resulting δ-hydroxy-β-keto- ester XI to the β-keto-δ-lactone XII, catalytically hydrogenation the latter and converting the resulting β-hydroxy-δ-lactone II into an ester I via the compounds of formulae III to VII according to the procedure described above.

The manufacture of the ester of formula I in which $R^1$ is n-hexyl and $R^2$ is undecyl is especially preferred.

The following β-hydroxy-δ-lactones, β-keto-δ-lactones and pyrones, which fall under formulae II, XII or XVI as the case may be, are novel and as such are objects of the present invention:

rac-(2RS,3RS,5SR)-2-Hexyl-3-hydroxy-5-undecyl-δ-valeriolactone,
rac-(2RS,3RS,5SR)-2-ethyl-5-heptadecyl-3-hydroxy-δ-valeriolactone,
(2S,3S,5R)-2-ethyl-5-heptadecyl-3-hydroxy-δ-valeriolactone and
rac-(2RS,3RS,5SR)-2-hexyl-3-hydroxy-5-pentyl-δ--valeriolactone;
rac-5,6-dihydro-3-hexyl-4-hydroxy-6-undecyl-2H-pyran-2-one,
(R)-3-ethyl-5,6-dihydro-6-heptadecyl-4-hydroxy-2H-pyran-2-one and
rac-5,6-dihydro-3-hexyl-4-hydroxy-6-pentyl-2H-pyran-2-one,
3-hexyl-4-hydroxy-6-undecyl-2-one,
3-ethyl-6-heptadecyl-4-hydroxy-2H-pyran-2-one and
3-hexyl-4-hydroxy-6-pentyl-2H-pyran-2-one.

The β-keto-δ-lactones of formula XXI in which $R^2$ has the significance given above, but the number of C atoms in the alkyl group $R^2$ amounts to more than 9, especially the following:
(R)-5,6-dihydro-6-undecyl-2H-pyran-2,4(3H)-dione and
(R)-5,6-dihydro-6-heptadecyl-2H-pyran-2,4(3H)-dione, are also novel and are an object of the invention.

The following Examples serve to illustrate the present invention in more detail. They are, however, not intended to limit its scope in any manner. The Examples below were carried out as written unless otherwise stated. All temperatures are degrees Celsius.

EXAMPLE 1 a) 465 g of methyl acetoacetate were added dropwise under nitrogen and stirring to 720 g of 30% sodium methylate solution in 1200 ml of methanol. Then, 727 g of 1-bromohexane were added and the reaction mixture was boiled at reflux for 20 hours. The majority of the methanol was distilled off and the residue was poured on to ice-water. The mixture was extracted with n-hexane and then with water. The organic phases were combined and dried over sodium sulphate. The solvent was evaporated and the crude ester was distilled. There were obtained 499.4 g of methyl 2-acetyloctanoate, b.p. 124°–128°/15 Torr.

b) 200.3 g of methyl 2-acetyloctanoate were added to a suspension of 26.4 g of sodium hydride in 1250 ml of THF. After stirring at 0°–5° for 1 hour the mixture was cooled to −10°. 675 ml of 1.56M butyllithium in hexane were added at this temperature. After stirring at −10° for 30 minutes 107.2 g of methyl laurate were added dropwise. The mixture was stirred at −10° for a further 1 hour. The reaction solution was added under argon to 250 ml of 37% hydrochloric acid and 300 g of ice. The mixture was extracted with hexane and water. The combined organic phases were dried, filtered and evaporated.

The residue (290.5 g) was dissolved in 1250 ml of toluene, treated with 76.1 g of DBU and boiled at reflux under argon for 30 minutes. The reaction solution was extracted in toluene with 3N hydrochloric acid and water. The combined toluene phases were evaporated at 40°. The product was dissolved in hexane and cooled to room temperature while stirring. After stirring at −10° for 17 hours the crystallizate was filtered off under suction, washed with hexane and dried. 123.9 g (70.7%) of 3-hexyl-4-hydroxy-6-undecyl-2H-one, m.p. 83°–84°, resulted.

c) 100 g of Raney-nickel and 2000 ml of ethyl acetate were added to 100 g of the pyrone from b). After hydrogenating for 17 hours while stirring at 30° the catalyst was filtered off under suction and washed with ethyl acetate. The filtrate was concentrated and stirred at −10° overnight. The crystallizate was filtered off under suction, washed with ethyl acetate and then dried. 90.7 g (89.7%) of rac-(2RS,3RS,5SR)-2-hexyl-3-hydroxy-5-undecyl-δ-valerolactone, m.p. 98°–99°, resulted.

d) 177.3 g of the δ-lactone from c) were suspended in 1250 ml of toluene while stirring. After the addition of 138.6 g of benzoic anhydride the mixture was stirred for 10 minutes. Then, 2.5 ml of perchloric acid were added. The mixture was stirred for a further 2.5 hours. The reaction solution was extracted in toluene with 1N sodium hydroxide solution and then with water. The combined toluene phases were dried, the drying agent was filtered off under suction and washed with toluene. Evaporation of the solvent gave 237.2 g (103.4%) of rac-(2RS,3RS,5SR)-3-benzoyloxy-2-hexyl-5-undecyl-δ-valerolactone, which was used in the next step without purification.

e) 236 g of the benzoate from d) in 1250 ml of methanol were treated under argon while stirring with 2.5 ml of conc. sulphuric acid and stirred for a further 18 hours. Subsequently, the pH of the reaction solution was adjusted to 9 with triethylamine and the methanol was evaporated. The residue was taken up in hexane, washed with water and the aqueous phase was extracted with hexane. After drying the combined hexane phases were filtered. The filtrate was freed from hexane. There resulted 259 g (105.5%) of methyl rac-(2RS,3RS,5SR)-3-benzoyloxy-2-hexyl-5-hydroxyhexadecanoate, which was used in the next step without purification.

f) 258 g of the hydroxyester from e) in 1250 ml of hexane were treated under argon while stirring with 152 g of benzyl 2,2,2-trichloroacetimidate. Then, 3.2 ml of trifluoromethanesulphonic acid were added. After stirring for 17 hours the precipitate was filtered off under suction and washed with hexane. The filtrate was extracted with 5% sodium bicarbonate solution and then with water. The hexane phase was dried, filtered and evaporated. 320 g (110%) of methyl rac-(2RS,3RS,5SR)-3-benzoyloxy-5-benzyloxy-2-hexylhexadecanoate resulted.

g) 319 g of the benzyl ether from f) in 1125 ml of methanol were treated under argon with a solution of 140 g of potassium hydroxide in 125 ml of water. The reaction mixture was stirred at 40° for 17 hours and subsequently concentrated. The suspension, together with n-hexane, was extracted with 10% sodium chloride solution and then 1N hydrochloric acid. The combined organic phases were dried with sodium sulphate, the drying agent was filtered off under suction and washed with hexane. The filtrate was concentrated to 1000 ml and held at −20° for 1 day. The crystallizate was filtered off under suction, washed with n-hexane and discarded. After evaporation the filtrate gave 169 g (73%) of rac-(2RS,3RS,5SR)-5-benzyloxy-2-hexyl-3-hydroxyhexadecanoic acid.

h) 39.4 g of (S)-(−)-α-methylbenzylamine were added dropwise under argon while stirring to 169 g of the δ-hydroxyacid from g) in 1250 ml of methyl acetate. The solution was seeded with phenethylamine salt and then cooled to −10°. After 17 hours at −10° the crystal slurry was filtered off under suction, washed with methyl acetate, sucked off and dried. After two additional crystallizations from methyl acetate there were obtained 56.5 g (19.4%) of the phenethylamine salt of (2S,3S,5R)-5-benzyloxy-2-hexyl-3-hydroxyhexadecanoic acid, m.p. 104°-105°.

i) 56.5 g of the phenethylamine salt from h) were treated with 565 ml of hexane and 120 ml of 1N hydrochloric acid while stirring. The organic phase was washed with water, dried and concentrated. There were obtained 44.2 g (98.8%; 19.1% based on the δ-lactone from c)) of (2S,3S,5R)-5-benzyloxy-2-hexyl-3-hydroxyhexadecanoic acid.

j) 231.5 g of the δ-hydroxyacid from i) were dissolved in 2500 ml of pyridine while stirring and cooled to 0°. Now, 176.6 g of benzenesulphonyl chloride were added dropwise. The solution was stirred at 0° for a further 20 hours. Thereafter, water was added and the mixture was stirred at room temperature for 30 minutes. The pyridine was evaporated. The crystal slurry, together with hexane, was extracted in succession with 2N hydrochloric acid, 5% sodium bicarbonate solution and 10% sodium chloride solution. The hexane phases were combined and concentrated. After drying active charcoal was added, the mixture was stirred for 1 hour, suction filtered, washed with hexane and evaporated. There resulted 222.1 g (99.9%) of (3S,4S)−4-[(R)-2-benzyloxytridecyl]-3-hexyl-2-oxetanone, which was used in the next step without purification.

k) 222 g of the β-lactone from j) were dissolved in 2500 ml of THF and hydrogenated on 11 g of Pd/C 10% for 18 hours. The solution was filtered and washed with THF. The filtrate was evaporated. The crystals obtained were dissolved in hexane. After stirring at 5° for 18 hours the crystallizate was filtered off under suction, washed with hexane and dried. 150.5 g (84.9%) of (3S,4S)-3-hexyl-4-[(R)-2-hydroxytridecyl]-2-oxetanone, m.p. 61°-62° C., were obtained.

EXAMPLE 2

88.6 g of the hydroxy-β-lactone from Example 1k), 51.7 g of N-formyl-(S)-leucine and 98.4 g of triphenylphosphine were dissolved in 1000 ml of THF while stirring. A solution of dropwise to the solution which was cooled to −10° C. The reaction solution was stirred at −10° C. for 15 hours. Subsequently, the solvent was evaporated. The crystal slurry was partitioned several times between hexane and 70% methanol water while stirring. The combined hexane phases were dried over sodium sulphate, the drying agent was filtered off under suction and washed with hexane. After distillation of the hexane the crude product was dissolved in hexane and cooled slowly to 5°. The crystallizate was filtered off under suction, washed with hexane and dried. 98.0 g of N-formyl-L-leucine-(S)−1-[[(2S,3S)-3-hexyl-4-oxo-2-oxetanyl]-methyl]-dodecyl ester, m.p. 44°-45° C., were obtained.

EXAMPLE 3 a) A suspension of 206.7 g of methyl (R)-3-hydroxytetradecanoate in 1000 ml of cyclohexane was treated under nitrogen and while stirring with 214.2 g of benzyl trichloroacetimidate and dissolved at 20°. 10 ml of trifluoromethanesulphonic acid were added dropwise while cooling in an ice/water bath in such a manner that the temperature remains between 20°-23°. The resulting suspension was stirred at 25°-30°. The precipitate was filtered off, the filter cake was washed with cyclohexane, the filtrates were extracted with sat. NaHCO₃ solution, water and sat. NaCl solution. The organic phase was dried over magnesium sulphate, filtered, the filter cake was washed with cyclohexane and the filtrates were evaporated. 314.5 g of methyl (R)-3-(benzyloxy)-tetradecanoate were obtained.

b) 314.0 g of the methyl ester from a) were added to a solution of 89.8 g of potassium hydroxide in 680 ml of methanol. After stirring at room temperature for 18.5 hours the resulting suspension was poured on to 680 g of ice and adjusted to pH 1 with 200 ml of 25 percent aqueous HCl solution while cooling at 0°-7°. The resulting emulsion was extracted with methylene chloride. The organic phase was dried over magnesium sulphate, filtered, the filter cake was washed with methylene chloride and the filtrates were evaporated. 277.3 g of (R)-3-benzyloxytetradecanoic acid were obtained.

c) 82.5 ml of oxalyl chloride were added dropwise to a solution of 276.5 g of the acid from b) in 1400 ml of methylene chloride. After stirring for 3.5 hours the resulting solution of (R)-3-benzyloxytetradecanoyl chloride was concentrated to 450 ml.

d) 164 ml of pyridine were added dropwise at −6° to 0° to a solution of 122.8 g of Meldrum acid in 900 ml of methylene chloride. After stirring at −3° to −1° for 10 minutes the solution of the acid chloride from c) was added dropwise. The resulting suspension was stirred at 0° for 3 hours, then poured into a mixture of 400 g of ice and 1300 ml of hydrochloric acid, stirred for 10 minutes, the organic phase was separated and extracted with 300 ml of 3N hydrochloric acid. The acidic-aqueous phases were extracted with 500 ml of methylene chloride, the combined organic phases were dried over magnesium sulphate, filtered, the filter cake was washed with methylene chloride and the filtrates were concentrated. The solution was treated with silica gel and stirred. The silica gel was filtered off and washed with methylene chloride. The filtrates were concentrated. 382.2 g of 5-[(R)-3-benzyloxy-1-hydroxytetradecylidene]-2,2-dimethyl-m-dioxane-4,6-dione were obtained.

e) 33.1 of 5Pd/C were added to a solution of 381.5 g of the product from d) in 2500 ml of ethyl acetate. The mixture was hydrogenated for 3.5 hours. The suspension was filtered, the filter cake was washed with ethyl acetate and the filtrates were concentrated. The solution obtained was boiled at 79°-80°, cooled to room temperature, evaporated and dried. The product was suspended in n-hexane, filtered and the filter cake was washed with n-hexane and the crystals were dried. The mother liquor was concentrated, dissolved in n-hexane and left to stand at 4° for 72 hours. The precipitated crystals were filtered, washed with n-hexane and dried. The two crystallizates were combined, suspended in water, stirred, filtered, the filter cake was washed with water and the crystals were dried. 62.1 g of (R)-5,6-dihydro-6-undecyl-2H-pyran-2,4(3H)-dione, m.p. 82°-85°, were obtained.

f) 100.65 g of the pyrandione from e) were added under nitrogen to a solution of 43.14 g of borane-triethylamine complex in 1000 ml of methanol. The mixture was warmed to 40°. 75.12 g of capronaldehyde were added dropwise to the solution. The solution was stirred at 41° for 70 minutes, then cooled to room temperature and poured on to ice-water. The suspension was treated with 120 ml of 3N hydrochloric acid while stirring and stirred for 30 minutes. The crystals were filtered off under suction, washed with water and then dried. The product was suspended in n-hexane, stirred for 30 minutes, filtered off under suction, washed with n-hexane and dried. There were obtained 112.5 g (85%) of (R)-5,6-dihydro-3-hexyl-4-hydroxy-6-undecyl-2H-pyran-2-one, m.p. 106°-108°, $[\alpha]_D^{20} = -45.6°$ (c=1% in dioxan).

g) 30.0 g of the pyranone from f) were dissolved in 750 ml of ethyl acetate and, after the addition of 30 g of Raney-nickel, hydrogenated at room temperature for 24.5 hours. The catalyst was filtered, washed with ethyl acetate and the filtrate was concentrated. The product was dissolved in ethyl acetate at 45°, cooled to 20° within 2 hours, then to −10° within 3 hours and stirred at this temperature for 16 hours and then filtered. The crystals were washed with ethyl acetate and then dried. There were obtained 25.5 g (85%) of (2S,3S,5R)-2-hexyl-3-hydroxy-5-undecyl-δ-valerolactone, m.p. 103°-104.5°, $[\alpha]_D^{20} = +47.4°$ (c=1% in CHCl$_3$).

h) A solution of 12.0 g of the lactone from g) in 70 ml of DMF was treated with 6.77 g of ethyl diisopropylamine and, after the addition of 7.64 g of t-butyldimethylsilyl chloride, heated to 80° for 13 hours while stirring. The reaction mixture was concentrated, taken up in 120 ml of hexane, filtered and the filter cake was washed with 50 ml of hexane. The combined filtrates were extracted with 3N hydrochloric acid and the organic phase was dried. After filtration and concentration there were obtained 15.7 g of (2S,3S,5R)-3-t-butyldimethylsiloxy-2-hexyl-5-undecyl-δ-valerolactone.

i) A solution of 42.2 g of the lactone from h) in 570 ml of dioxan was stirred for 5.5 hours after the addition of 90 ml of 1N potassium hydroxide solution. The reaction mixture was concentrated and dried azeotropically by the addition of toluene and distillation. The residue was dissolved in 250 ml of THF and, after the addition of 23.1 g of benzyl bromide and 4.75 g of 18-crown-6, stirred for 4 hours. The reaction mixture was concentrated, treated with n-hexane and extracted with 3N hydrochloric acid. The organic phase was dried, filtered and concentrated, whereby 61.7 g of benzyl(2S,3S,5R)-3-t-butyldimethylsiloxy-2-hexyl-5-hydroxyhexadecanoate separated.

j) A solution of 60.6 g of the product from i) in 130 ml of methylene chloride and 260 ml of cyclohexane was treated with 33.5 g of benzyl trichloroacetimidate and, after the addition of 0.53 ml of trifluoromethanesulphonic acid, stirred for 5 hours. The suspension was filtered, the filter cake was washed with hexane and the combined filtrates were washed in sequence with 3N hydrochloric acid, 3N sodium hydroxide solution, 3N hydrochloric acid and water. The organic phase was dried, filtered and concentrated, whereby 74.8 g of benzyl (2S,3S,5R)-5-benzyloxy-3-t-butyldimethylsiloxy-2-hexylhexadecanoate separated.

k) A mixture of 20 g of the ester from j), 48 ml of glacial acetic acid, 16 ml of water and 16 ml of dioxan was heated at reflux for 3.5 hours and subsequently freed from the acetic acid by azeotropic distillation with the addition of 120 ml of dioxan and concentrated. The residue was dissolved in hexane and stored at −25° for 14 hours. The crystals formed were filtered, the filtrate was concentrated and the residue, dissolved in methanol, was mixed thoroughly for 24 hours with an aqueous solution of potassium hydroxide. The reaction solution was evaporated, the residue was taken up in hexane and washed with 1N hydrochloric acid and 10% sodium chloride solution and concentrated. The residue was dissolved in methyl acetate and treated with 2.6 g of benzylamine. By crystallization there were obtained 6.0 g of (2S,3S,5R)-5-benzyloxy-3-hydroxy-2-hexylhexadecanoic acid (the product of Example 1h)) as the benzylamine salt of m.p. 57°-60° and a further 1.4 g of m.p. 61°-64°.

EXAMPLE 4 a) Under nitrogen and while stirring there were added dropwise to a solution of 129.2 g of methyl (R)-3-hydroxytetradecanoate, 1033 ml of dioxan and 122.9 g of 28 percent sodium hydroxide solution. 77.5 ml of methanol were added dropwise to the solution. After stirring for a further 1.5 hours the resulting suspension was filtered and the filter cake was washed with 1000 ml of dioxan and filtered off. The filter cake was adjusted to pH 0 by the addition of 650 ml of 1.5N hydrochloric acid. The suspension was stirred, filtered, the filter cake was washed with 3000 ml of water and the crystals were dried. 119.64 g (98%) of (R)-3-hydroxytetradecanoic acid, m.p. 70.6°-71.4°, were obtained.

b) 5.11 g of magnesium chloride were suspended in 50 ml of THF under nitrogen and cooled to 0°. A solution of 11.33 g of monomethyl malonate in 70 ml of THF and subsequently 10.7 g of triethylamine were added dropwise. The suspension was stirred at 0°.

c) 6.81 g of 1,1'-carbonyldiimidazole were added under nitrogen and while stirring to a solution of 7.33 g of (R)-3-hydroxytetradecanoic acid.

d) The reaction solution obtained under c) was added to the suspension previously prepared under b) and stirred for 5 hours. The suspension was concentrated. The resin obtained was taken up in 200 ml of ethyl acetate and extracted with 3N hydrochloric acid. The ethyl acetate phase was treated with 3N sodium hydroxide solution and, after the addition of ice-water, the aqueous phase was separated. The ethyl acetate phase was again mixed thoroughly with 3N sodium hydroxide solution, diluted with ice-water and extracted. The combined aqueous phases were cooled to 0° and adjusted to pH 1 with 25 percent hydrochloric acid. The resulting suspension was extracted with ethyl acetate. The combined organic phases were dried and filtered. The filter cake was washed with ethyl acetate. The combined filtrates were concentrated. The product was suspended in ice-water, stirred and filtered. The filter cake was washed with water and the crystals were dried. There were obtained 4.63 g (57.6%) of (R)-5,6-dihydro-6-undecyl-2H-pyran-2,4(3H)-dione, m.p. 84.1°–84.8°, the product of Example 3e).

EXAMPLE 5 a) 350.1 g of 30 percent sodium methylate solution in methanol were diluted with 550 ml of methanol under nitrogen and while stirring. 264.2 g of dimethyl malonate were added dropwise. After warming the suspension to 40° 321.0 g of 1-bromohexane were added dropwise. After stirring at 40° for 1 hour, under reflux for 2 hours, at 65°–69° for 2.5 hours and cooling the suspension to room temperature water was added and the mixture was stirred. The organic phase was separated. The aqueous phase was extracted with methylene chloride, the combined organic extracts were dried and filtered, the filter cake was washed with methylene chloride and the combined filtrates were concentrated. After distillation of the product there were obtained 329.3 g (78.3%) of dimethyl n-hexylmalonate.

b) A solution of 40.1 g of KOH in 150 ml of methanol was added dropwise under nitrogen and while stirring to 129.78 g of the ester from a). The reaction mixture was stirred for 2 hours, then poured on to ice-water and extracted with methylene chloride. The aqueous phase was adjusted to pH 2 by the addition of 3N hydrochloric acid and extracted with methylene chloride. The organic phases were dried and filtered, the filter residue was washed with methylene chloride and the combined filtrates were concentrated. 113.9 g (94%) of monomethyl n-hexylmalonate were obtained.

c) A solution of 21.57 g of the ester from b) in 70 ml of THF and subsequently 10.7 g of triethylamine were added dropwise under nitrogen and while stirring to a suspension of 5.11 g of magnesium chloride in 50 ml of THF at 0° and the resulting suspension of monomethyl n-hexylmalonate magnesium salt was stirred at 0° for 75 minutes.

d) 6.81 g of 1,1'-carbonyldiimidazole were added under nitrogen and while stirring to a solution of 7.33 g of (R)-3-hydroxytetradecanoic acid (Example 4a) in 60 ml of THF. After stirring the reaction solution was added to the suspension of monomethyl n-hexylmalonate magnesium salt and the mixture was stirred at room temperature for 22 hours. The suspension was concentrated, whereby 60.35 g of resin remained behind. This was taken up in 200 ml of ethyl acetate, extracted with 200 ml of 3N hydrochloric acid and with 600 ml of 5 percent NaHCO$_3$ solution. The ethyl acetate phase was separated and treated with 100 ml of 25 percent hydrochloric acid while stirring at 10°–15°. The mixture was stirred at 25° for 1.5 hours. The resulting, homogeneous phase was left to stand at room temperature for 16 hours. The suspension was stored at −20° for 4 hours, filtered, the filter cake was washed with water and the crystals were dried. There were obtained 3.63 g (34.3%) cf (R)-5,6-dihydro-3-hexyl-4-hydroxy-6-undecyl-2H-pyran-2-one, m.p. 104.8°–106.2°, the product of Example 3f).

EXAMPLE 6 a) 465 g of methyl acetoacetate and then 458 g of ethyl bromide were added under nitrogen to 720 g of 30% sodium methylate solution in 1200 ml of methanol. The reaction mixture was subsequently boiled at reflux. After distillation of the methanol the residue was poured on to ice-water. It was then extracted with n-hexane and water. The organic phases were combined and dried. After evaporation of the solvent and distillation there were obtained 328 g (56.9%) of methyl 2-acetylbutyrate, b.p. 77°–79°/15 Torr.

b) 144.17 g of the methyl ester from a) were added under argon at 0°–5° to a suspension of 26.4 g of sodium hydride in 1250 ml of THF. After stirring at 0°–5° for 1.5 hours the mixture was cooled to −10°. 675 ml of 1.56M butyllithium in hexane were added at this temperature. After stirring at −10° for 30 minutes a solution of 149.3 g of methyl stearate in 250 ml of THF was added dropwise. After stirring at −10° for 1.5 hours the reaction solution was added under argon to 250 ml of 37% hydrochloric acid and 300 g of ice. The mixture was extracted with hexane and water. The combined organic phases were dried, filtered and evaporated.

The residue was dissolved in 2500 ml of THF, treated with 76.1 g of DBU and boiled at reflux under argon. The cooled reaction solution was extracted with 37% hydrochloric acid and then with saturated sodium chloride solution. The combined organic phases were dried and evaporated. The product was dissolved in ethyl acetate. The solution was cooled to room temperature and stirred at 25° overnight. The crystallizate was filtered off under suction, washed with ethyl acetate and dried. 122.5 g (64.7%) of 3-ethyl-δ-heptadecyl-4-hydroxy-2H-pyran-2-one, m.p. 101°–102°, resulted.

c) 100 g of Raney-nickel and 2000 ml of THF were added to 100 g of the pyrone from b). After hydrogenation at 25° for 3 days the catalyst was filtered off under suction and washed with THF. The filtrate was evaporated to dryness. The residue was dissolved in ethyl acetate and stirred at 10° for 17 hours. The crystallizate was filtered off under suction, washed with −10° cold ethyl acetate and dried at 40° for 17 hours. 90.54 g (89.6%) of rac-(2RS,3RS,5SR)-2-ethyl-5-heptadecyl-3-hydroxy-δ-valerolactone, m.p. 101°–102°, resulted.

d) 138.5 g of benzoic anhydride and subsequently 2.5 ml of perchloric acid 70% were added to a suspension of 191.3 g of the δ-lactone from c) in 1250 ml of toluene. After stirring for 2.5 hours the reaction mixture in toluene was extracted with 1N sodium hydroxide solution in 20% sodium chloride solution and then with saturated sodium chloride solution. The organic phases were combined, dried and evaporated. 243.4 g (100.0%) of rac-(2RS,3RS,5SR)-3-benzoyloxy-2-ethyl-5-heptadecyl-δ-valerolactone, m.p. 64.5°–66°, resulted.

e) 243 g of the benzoate from d) were dissolved in 450 ml of toluene at 40° under argon. 1000 ml of methanol and thereafter 2.5 ml of conc. sulphuric acid were added and the reaction mixture was stirred at 25° for 20 hours. After neutralization of the sulphuric acid with triethylamine the solvent was evaporated. The residue was dissolved in t-butyl methyl ether and washed with water. The aqueous phase was extracted with t-butyl methyl ether and the organic phases were combined and dried over sodium sulphate, the drying agent was filtered off under suction and washed with t-butyl methyl ether and subsequently evaporated. 257 g (99.1%) of methyl rac-(2RS,3RS, 5SR)-3-benzoyloxy-2-ethyl-5-hydroxydocosanoate resulted.

f) 257 g of the hydroxyester from e) in 1250 ml of n-hexane were treated under argon with 152 g of benzyl 2,2,2-trichloroacetimidate. Then, 3.2 ml of trifluoromethanesulphonic acid were added. After stirring at room temperature for 18 hours the precipitate was filtered off under suction and washed with n-hexane. The filtrate was extracted with 5% sodium bicarbonate solution and water. The combined hexane phases were dried, filtered and concentrated. After stirring at −20° for 20 hours the crystallizate was filtered off under suction, washed with n-hexane and discarded. The filtrate was evaporated. There resulted 239.6 g (78.7%) of methyl rac-(2RS,3RS,5SR)-3-benzoyloxy-5-benzyloxy-2-ethyl-docosanoate, the next step without purification.

g) 239.6 g of the benzyl ether from f) were treated under argon with a solution of 140 g of potassium hydroxide in 1250 ml of 95% (v/v) methanol/water and stirred at 40° for 17 hours. Subsequently, the mixture was concentrated at 40°. The suspension was taken up in t-butyl methyl ether and washed in sequence with 10% sodium chloride solution, 1N hydrochloric acid and again with 10% sodium chloride solution. The organic phase was dried with sodium sulphate, the drying agent was filtered off under suction and washed with t-butyl methyl ether. The filtrate was evaporated. 182.1 g (74.2%) of rac-(2RS,3RS,5SR)-5-benzyloxy-2-ethyl-3-hydroxydocosanoic acid resulted.

h) 33.3 g of (S)-(−)-α-methylbenzylamine were added dropwise to a solution of 182.1 g of the β-hydroxyacid from g) in 1250 ml of methyl acetate. The solution was seeded with 50 mg of the phenethylamine salt of (2S,3S,5R)-5-benzyloxy-2-ethyl-3-hydroxydocosanoic acid and left to stand for 20 hours. The crystallizate was filtered off under suction, washed with −20° cold methyl acetate and then dried. This 1st crystallizate was dissolved in hot methyl acetate, cooled to 45° and seeded with 50 mg of the phenethylamine salt of (2S,3S,5R)-5-benzyloxy-2-3-hydroxydocosanoic acid. The solution was left to stand at room temperature for 20 hours. The crystallizate was filtered off under suction, washed with −20° cold methyl acetate and dried. The same procedure as with the 1st crystallizate was repeated with the 2nd crystallizate. 39.4 g (12.9%) of the phenethylamine salt of (2S,3S,5R)-5-benzyloxy-2-ethyl-3-hydroxydocosanoic acid, m.p. 92°–95°, resulted.

i) 39.4 g of the phenethylamine salt from h) were treated with 400 ml of t-butyl methyl ether and 80 ml of 1N hydrochloric acid and dissolved while stirring. The organic phase was washed with water, dried, filtered and concentrated. 31.4 g (99.4%; 12.8% based on the δ-lactone from c) of (2S,3S,5R)-5-benzyloxy-2-ethyl-3-hydroxydocosanoic acid, m.p. 62°–63.5°, resulted.

j) 17.6 g of benzenesulphonyl chloride were added dropwise under argon to a solution of 24.5 g of the β-hydroxyacid from i) in 250 ml of pyridine at 0°. After stirring at 0° for 20 hours 5 ml of water were added dropwise to the solution. The mixture was stirred at room temperature for 1 hour. The pyridine was evaporated. The crystal slurry was taken up in t-butyl methyl ether and washed in succession with 2N hydrochloric acid, 5% sodium bicarbonate solution and 10% sodium chloride solution. The organic phase was dried over sodium sulphate and thereafter triturated with active charcoal. Drying agent and active charcoal were filtered off under suction and the filtrate was evaporated. 23.4 g (99%) of (3S,4S)-4-[(R)-2-benzyloxynonadecyl]-3-ethyl-2-oxetanone resulted.

k) A solution of 23.4 g of the oxetanone from j) in 250 ml of THF was treated with 2.3 g of Pd/C 10%. After hydrogenation for 5 hours the hydrogenation solution was suction filtered. After washing with THF the filtrate was evaporated, the residue was dissolved in n-hexane and seeded with (3S,4S)-3-ethyl-4-[(R)-2-hydroxynonadecenyl]-2-oxetanone. After 18 hours the crystallizate was filtered off under suction, washed with hexane and dried. 16.1 g (84.1%) of (3S,4S)-3-ethyl-4-[(R)-2-hydroxynonadecyl]-2-oxetanone, m.p. 66.5°–68°, resulted.

EXAMPLE 7

19.13 g of the hydroxy-β-lactone from Example 6k), 10.34 g of N-formyl-(S)-leucine and 19.70 g of triphenylphosphine were dissolved in 400 ml of THF under argon while stirring. The mixture was cooled to 0° and a solution of 14.5 g of diethyl azodicarboxylate in 50 ml of THF was added dropwise. The reaction solution was stirred at 0° for 4 hours. Subsequently, the solvent was evaporated. The crystal slurry was partitioned several times between hexane and 70% methanol/water. The combined hexane phases were dried over sodium sulphate, the drying agent was filtered off under suction and washed with hexane. After distillation of the hexane the product was dissolved in hexane and, after 20 hours, the crystallizate was filtered off under suction, washed with hexane and dried. 0.74 g (79.2%) of N-formyl-L-leucine-(S)-1-[[(2S,3S)-3-ethyl-4-oxo-2-oxetanyl]methyl]octadecyl ester, m.p. 61°–62°, resulted.

EXAMPLE 8 a) To a suspension of 177.3 g of (2S,3S,5R)-2-hexyl-3-hydroxy-5-undecyl-δ-valerolactone in 1250 ml of toluene under argon were added 135.7 g of benzoic anhydride and, after stirring at room temperature for 10 minutes, 2.5 ml of 70% perchloric acid. After stirring for 4 hours the reaction solution in toluene was extracted with 1N sodium hydroxide solution and water. The combined toluene phases were dried over sodium sulphate, the drying agent was filtered off under suction and washed with toluene. Evaporation of the solvent gives 249.9 g (109%) of (2S,3S,5R)-3-benzoyloxy-2-hexyl-5-undecyl-δ-valeriolactone, which was used in the next step without purification.

b) 249.8 g of the benzoate from a) in 1250 ml of methanol were treated under argon while stirring with 2.5 ml of conc. sulphuric acid and stirred at 35° for 18 hours. Subsequently, the pH value of the reaction solution was adjusted to 9 with triethylamine and the methanol was evaporated. The residue was taken up in hexane, washed with water and the aqueous phase was extracted with hexane. After drying the combined hexane phases they were filtered and the filtrate was freed from hexane. There resulted 246.5 g (100.5%) of methyl (2S,3S,5R)-3-benzoyloxy-2-hexyl-5-hydroxyhexadecanoate, which was used in the next step without purification.

c) 246.5 g of the hydroxyester from b) in 1250 ml of hexane were treated under argon while stirring with 152 g of benzyl 2,2,2-trichloroacetimidate. Then, 3.2 ml of trifluoromethanesulphonic acid were added. After stirring at room temperature for 17 hours the precipitate was filtered off under suction and washed with hexane. The filtrate was extracted with 5% sodium bicarbonate solution and then with water. The combined hexane phases were dried, filtered and evaporated. There resulted 308 g (106.2%) of methyl (2S,3S,5R)-3-benzoyloxy-5-benzyloxy-2-hexylhexadecanoate, which was used in the next step without purification.

d) 308.5 g of the benzyl ether from c) in 1125 ml of methanol were treated under argon with a solution of 140 g of potassium hydroxide in 125 ml of water. The reaction mixture was stirred at 40° for 17 hours and subsequently concentrated. The suspension was taken up in hexane and washed in sequence with 10% sodium chloride solution, 1N hydrochloric acid and 10% sodium chloride solution. The organic phase was dried with sodium sulphate, the drying agent was filtered off under suction and washed with hexane. The filtrate was concentrated to 1000 ml and stirred at −20°. The crystallizate was filtered off under suction, washed with hexane and discarded. After evaporation of the solvent the filtrate gave a product which was dissolved in methyl acetate and treated with benzylamine while stirring. The solution was seeded with the benzylamine salt of (2S,3S,5R)-5-benzyloxy-2-hexyl-3-hydroxyhexadecanoic acid and subsequently cooled to −5°. Then, it was crystallized at −10° for 17 hours. The crystallizate was filtered off under suction, washed with methyl acetate and thereafter dried. 116.7 g (41% based on the starting valerolactone of a) of the benzylamine salt of (2S,3S,5R)-5-benzyloxy-2-hexyl-3-hydroxy-hexadecanoic acid, m.p. 66°–68°, resulted.

e) 116.7 g of the benzylamine salt from d) were treated with 1000 ml of hexane and 250 ml of 1N hydrochloric acid while stirring. The organic phase was washed with water, dried and evaporated. There were obtained 95.4 g (100.6%; 41.2% based on the starting valerolactone of a) of (2S,3S,5R)-5-benzyloxy-2-hexyl-3-hydroxyhexadecanoic acid, the product of Example 1i).

EXAMPLE 9 a) 110.2 g of methyl 2-acetyloctanoate (the product of Example 1a) were added dropwise under argon and while stirring at 0°–5° to a suspension of 14.4 g of sodium hydride 97% in 750 ml of THF. The mixture was stirred at room temperature for 1 hour and subsequently cooled to −12°. 370 ml of 1.56M butyllithium in hexane were added within 1 hour at −12 to −10°. The mixture was stirred at −12° for 1 hour. 92.2 g of lauric aldehyde were added dropwise at −10° to the solution obtained. The mixture was stirred at this temperature for a further 1 hour. The reaction solution was added to 600 ml of water within 5 minutes while stirring. The mixture was stirred at room temperature for a further 1 hour and subsequently neutralized with 100 ml of 37% hydrochloric acid. After separating the aqueous phase the organic phase was washed with 300 ml of saturated sodium chloride solution, dried over sodium sulphate and the drying agent was filtered off under suction. After evaporation of the solvent the product was triturated with hexane. The crystallizate was filtered off under suction, washed with hexane and dried. 130.61 g (74.1%) of rac-5,6-dihydro-3-hexyl-4-hydroxy-δ-undecyl-2H-pyran-2-one, m.p. 121.5°–122.5°, resulted.

b) 1000 ml of ethyl acetate and 12.5 g of Raney-nickel were added to 50 g of the dihydropyrone from a) while stirring. After hydrogenating for 17 hours while stirring at 30° the catalyst was filtered off under suction and washed with ethyl acetate. The filtrate was concentrated and stirred at −10°. The crystallizate was filtered off under suction, washed with ethyl acetate and dried. There resulted 45.4 g (90.3%) of rac-(2RS,3RS,5SR)-2-hexyl-3-hydroxy-5-undecyl-δ-valerolactone, m.p. 98.5°–99.5°, the product of Example 1c).

EXAMPLE 10 a) To a solution of 117 g of Meldrum's acid and 131 ml of pyridine in 1.5 l of methylene chloride, 270 ml of stearic acid chloride were added dropwise at a maximum temperature of 15° C. After stirring, the reaction mixture was washed with 4N hydrochloric acid, the aqueous phase was extracted with methylene chloride, the methylene chloride phase was dried and concentrated. The residue was taken up in methanol and stirred under reflux. After cooling, the precipitated crystals were filtered off, dissolved in methylene chloride and chromatographed on silica gel with methylene chloride to give 175 g of methyl-3-oxoeicosanoate, m.p. 52°–54° C.

b) To a solution of 9.1 mg of [(R)-2,2'-bis(diphenylphosphino)-6,6'-dimethylbiphenyl]ruthenium-diacetate in 20 ml of methylene chloride, were added 1.84 mg of acetyl chloride in 1.84 ml of methanol. The obtained solution was hydrogenated at 60° C. under 35 bar of hydrogen together with 39.8 mg of the ketoester of (a) and 170 ml of methanol. After adding methylene chloride, the mixture was evaporated to dryness. Chromatography on silica gel with diethyl ether and recrystallization from n-hexane gave 35.7 g of methyl (R)-3-hydroxyeicosanoate, m.p. 64°–64.5° C.

c) Analogously to Example 4, from methyl (R)-3-hydroxyeicosanoate via (R)-3-hydroxyeicosanoic acid of m.p. 89° there was prepared (R)-5,6-dihydro-δ-heptadecyl-2H-pyran--2,4(3H)-dione of m.p. 97°.

Analogously to Example 3f) and g), the above pyrandione was converted with acetaldehyde via (R)-3-ethyl-5,6-dihydro-6-heptadecyl-4-hydroxy-2H-pyran-2-one of m.p. 110.5°–112.5° into 2S,3S,5R-2-ethyl-5-heptadecyl-3-hydroxy-δ-valerolactone, $[\alpha]_D^{20} = -39.8°$ (c=1 in CHCl$_3$).

Analogously to Example 2h) to k), the above pyranone can be converted via (3S,4S,6R)-4-(t-butyldimethylsiloxy) --3-3,4,5,6-tetrahydro-6-heptadecyl-2H-pyran-2-one, benzyl (2S,3S, 5R)-3-(t-butyldimentylsiloxy)-2-ethyl-5-hydroxydocosanoate and benzyl (2S,3S,5R)-5-benzyloxy-3-(t-butyldimethylsiloxy)-2-ethyldocosanoate into (2S,3S,5R)-5-benzyloxy-3-hydroxy-2-ethyldocosanoic acid (the product of Example 6h)) as the benzylamine salt.

EXAMPLE 11 a) Analogously to Example 1b). methyl 2-acetyloctanoate (Example 1a)) was converted with methyl hexanoate into 3-hexyl-4-hydroxy-δ-pentyl-2H-pyran-2-one. m.p. 110.8°–111.7°.

b) Analogously to Example 9a), methyl 2-acetyloctanoate was converted with hexanal into rac-5,6-dihydro-3-hexyl-4-hydroxy-6-pentyl-2H-pyran-2-one, m.p. 137°-139°.

c) Hydrogenation of the pyranone from a) or b) analogously to Example 1c) or 9c) gave rac-(2RS,3RS, 5SR)-2-hexyl-3-hydroxy-5-pentyl-δ-valerolactone. m.p. 117°-118°.

d) Analogously to Example 1d) to k), the lactone from Example 11c) was converted via rac-(2RS,3RS,5SR)-3-benzoyloxy-2-hexyl-5-pentyl-δ-valerolactone,
methyl rac-(2RS,3RS,5SR)-3-benzoyloxy-2-hexyl-5-hydroxydecanoate,
methyl rac-(2RS,3RS,5SR)-3-benzoyloxy-5-benzyloxy-2-hexyl-decanoate,
methyl rac-(2RS,3RS,5SR)-5-benzyloxy-2-hexyl-3-hydroxy-decanoate,
(2S,3S,5R)-5-benzyloxy-2-hexyl-3-hydroxydecanoic acid (S)-α-methylbenzylamine salt, m.p. 116°-117°,
(2S,3S,5R)-5-benzyloxy-2-hexyl-3-hydroxydecaoic acid, $[\alpha]_D^{20} = -31.5°$ (c=0.635 in CHCl$_3$), and (3S,4S)-4-[(R)-2-benzyloxyheptyl]-3-hexyl-2-oxetanone, $[\alpha]_D^{20} = 63.1°$ (c=1 in CHCl$_3$),
into (3S,4S)-3-hexyl-4-[(R)-2-hydroxyheptyl]-2-oxetanone, $[\alpha]_D^{20} = -51.9°$ (c=1 in CHCl$_3$).

e) The latter was esterified analogously to Example 2 to N-formyl-L-valine-(S)-1-[[(2S,3S)-3-hexyl-4-oxo-2-oxetanyl]methyl]hexyl ester (valilactone), m.p. 57.0°-57.3°, or to N-formyl-L-leucine-(S)-1-[[(2S,3S)-3-hexyl-4-oxo-2-oxetanyl]methyl]hexyl ester, m.p. 50°-50.5°.

EXAMPLE 12 a) 3.55 g of rac-(2RS,3RS,5SR)-2-hexyl-3-hydroxy-5-undecyl-δ-valerolactone (Example 1c), 30 ml of TBME, 12.6 mg of pyridinium p-toluenesulphonate and 2.66 g of 95% 3,4-dihydro-2H-pyran were stirred at 50° for 20 hours. The solution was washed with aqueous NaCl solution and then dried. Evaporation of the solvent and drying give 4.41 g (100.5%) of (2RS,3RS,5SR)-2-hexyl-3-(tetrahydro-2H-pyran-2-yloxy)-5-undecyl-δ-valeriolactone, m.p. 39°-41°.

b) A solution of 4.41 g of the ether from a) in 30 ml of t-butyl methyl ether was treated with 10 ml of 2N sodium hydroxide solution and stirred for 20 hours. After separating the aqueous phase the organic phase was washed with 10 ml of 10%, aqueous NaCl solution and evaporated at 55°. The residue was dissolved in 30 ml of TBME and the solvent was again evaporated. A solution of the residue in 30 ml of THF was firstly evaporated and then dried. 4.81 g (100.5%) of the sodium salt of (2RS,3RS, 5SR)-2-hexyl-5-hydroxy-3-(tetrahydro-2H-pyran-2-yloxy)hexadecanoic acid resulted.

c) 4.80 g of the sodium salt from b) were treated under argon with 50 ml of THF, 2.57 g of benzyl bromide and 0.495 g of sodium hydride and stirred at 50° for 24 hours. The suspension was hydrolyzed to pH 0 with 10 ml of 2N hydrochloric acid, stirred at 50° for 2 hours and then the aqueous phase was separated. After washing with aqueous NaCl solution the organic phase was evaporated. There resulted 5.42 g of rac-(2RS,3RS,5SR)-5-benzyloxy-2-hexyl-3-hydroxyhexadecanoic acid, the product of Example 1g), which was resolved into its antipodes as in Example 1h).

EXAMPLE 13 a) 177.3 mg of rac-(2RS,3RS,5SR)-2-hexyl-3-hydroxy-5-undecyl-δ-valerolactone (Example 1c)), 750 ml of TBME, 86.7 g of 97% 3,4-dihydro-2H-pyran and 0.314 g of pyridinium p-toluenesulphone were stirred at 50° under argon for 20 hours. 500 ml of 2N sodium hydroxide solution were added to the reaction solution. After stirring at 50° for 2.5 hours the aqueous phase was separated and the organic phase was washed with 500 ml of 10% sodium chloride solution. salt slurry was cooled, treated under argon in succession with 152.7 g of benzyl bromide and 99.1 g of Na t-butylate and stirred at room temperature for 24 hours. After adding 750 ml of 2N hydrochloric acid and stirring at 50° for 22 hours the mixture was cooled, the aqueous phase was separated and the organic phase was washed with sodium chloride solution, dried and filtered. After evaporation of the solvent there were obtained 349.8 g of rac-(2RS,3RS,5SR)-5-benzyloxy-2-hexyl-3-hydroxydecanoic acid (the product of Examples 1g and 12c)).

c) In a variant of b), the product of a) was boiled on a water separator for 17 hours. The solvent was then distilled off. After drying there were obtained 253.4 g of the sodium salt of (2RS,3RS,5SR)-2-hexyl-5-hydroxy-3-(tetrahydro-2H-pyran-2-yloxy)hexadecanoic acid.

d) A solution of the product from c) in 2 l of THF was added to a suspension of 24.7 g of 97% NaH in 500 ml of THF and 131 g of benzyl bromide at 50° while stirring. After stirring for 22 hours 500 ml of 2N hydrochloric acid were added. After cooling the aqueous phase was separated and washed with sodium chloride solution. The resulting solution of the racemic hydroxyacid, rac-(2RS,3RS,5SR)-5-benzyloxy-2-hexyl-3-hydroxycecanoic acid (Example 13b)), was used for the racemate resolution (Example 1h)).

We claim:

1. A process for producing a compound having the formula

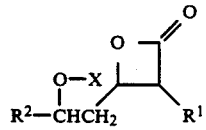

wherein $R^1$ and $R^2$ each are independently alkyl with up to 17 C atoms optionally interrupted by an O atom in a position other than the α- or β-position; or benzyl optionally ring-substituted by 1 or 3 $C_{1-6}$-alkyl or $C_{1-6}$-alkoxy groups, X is hydrogen or a group of the formula ($R^3$, $R^4$)NCH($R^5$)(CH$_2$)$_n$—CO—, $R^3$ is hydrogen, $C_{1-3}$-alkyl or $C_{1-3}$-alkanoyl, $R^4$ is hydrogen or $C_{1-3}$-alkyl and $R^5$ is hydrogen, a group Ar or Ar-$C_{1-3}$-alkyl or $C_{1-7}$-alkyl optionally interrupted by Y and optionally substituted by Z or $R^4$ with $R^5$ form together with the N atom to which they are attached to a 4- or 6-membered saturated ring, Y is oxygen, sulphur or a group N($R^6$) C(O)N($R^6$) or N($R^6$)C(O), Z is a group —(O or S)—$R^7$, —N($R^7$, $R^8$), —C(O)N($R^7$, $R^8$) or —N($R^7$)C(O))$R^8$, n is the number 1 or 0, whereby $R^5$ is hydrogen when n is the number 1, Ar is phenyl substituted by 1 to 3 groups $R^9$ or O$R^9$ and $R^6$ to $R^9$ are hydrogen or $C_{1-3}$-alkyl, and of salts of the compounds of formula I in which X is not hydrogen with weak acids, which process comprises the steps of:

a) etherifying a β-hydroxy-δ-lactone of the formula

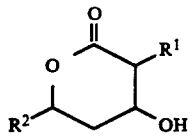
II b) opening the resulting ether of the formula

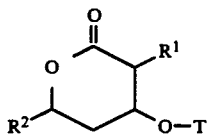
III wherein T is a readily cleavable ether group, with a base, c) reacting the resulting salt of the formula

wherein M is an alkali metal or alkaline earth metal, in optional sequence with an arylmethyl halide and a base and d) selectively cleaving the resulting diether of the formula $R^2$—CH(OCH$_2$—Ar)CH$_2$CH(O—T)CH($R^1$)C-OO—M    V with an acid, e) cyclizing the resulting β-hydroxyacid of the formula $R^2$—CH(OCH$_2$—Ar)CH$_2$CHOHCH($R^1$)COOH    VI optionally after resolution into its enantiomers, and f) cleaving the resulting β-lactone ether of the formula

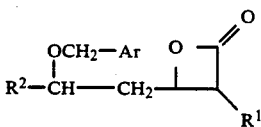
VII to form the compound of formula I, wherein X is hydrogen, and g) where a compound of formula I is required, wherein X is not hydrogen, esterifying the resulting β-lactone alcohol of formula I in which X is hydrogen with an agent which introduces the group X, and h) where a salt of a compound of formula I, wherein X is not hydrogen, is required, isolating the ester obtained in the form of a salt with a weak acid.

2. A process according to claim 1, wherein an alkali metal hydride is used as the base in step c).

3. A process according to claim 1 for producing a compound having the formula

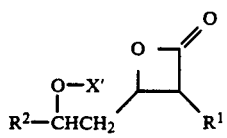
I' wherein wherein $R^1$ and $R^2$ each are independently alkyl up to 17 C atoms optionally interrupted by an O atom n a position other than and α- or β-position; or benzyl optionally ring-substituted by 1 to 3 $C_{1-6}$-alkyl or $C_{1-6}$-alkoxy groups, X' is a group of the formula ($R^3$, $R^4$)NCH($R^5$)(CH$_2$)$_n$—CO—, $R^3$ is hydrogen, $C_{1-3}$-alkyl or $C_{1-3}$-alkanoyl, $R^4$ is hydrogen or $C_{1-3}$-alkyl and $R^5$ is hydrogen, a group Ar or Ar-$C_{1-3}$-alkyl or $C_{1-7}$-alkyl optionally interrupted by Y and optionally substituted by Z or $R^4$ with $R^5$ form together with the N atom to which they are attached to a 4- or 6-membered saturated ring, Y is oxygen, sulphur or a group N($R^6$), C(O)N($R^6$) or N($R^6$)C(O), Z is a group —(O or S)—$R^7$, —N($R^7$, $R^8$), —C(O)N($R^7$, $R^8$) or —N($R^7$)C(O))$R^8$, n is the number 1 or 0, whereby $R^5$ is hydrogen when n is the number 1, Ar is phenyl substituted by 1 to 3 groups $R^9$ or O$R^9$ and $R^6$ to $R^9$ are hydrogen or $C_{1-3}$-alkyl, and of salts of the compounds of formula I in which X is not hydrogen with weak acids, which process comprises the steps of:

a) reacting a compound of the formula

CH$_3$COCH($R^1$)COO—R    XIII where R is $C_{1-4}$-alkyl with a compound of the formula

$R^2$—CHO    XVII to form a compound having the formula

$R^2$—CHOHCH$_2$COCH($R^1$)COO—R    XI, b) cyclizing the compound of formula XI to form a compound of the formula

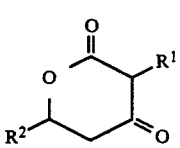
XII c) catalytically hydrogenating the compound of formula XII to form a compound of the formula

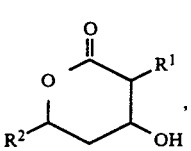
II d) etherifying the compound of formula II, e) opening the resulting ether of the formula

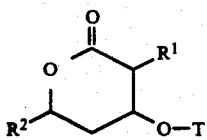

wherein T is a readily cleavable ether group, with a base, f) reacting the resulting salt of the formula $$R^2\text{—CHOHCH}_2\text{—CH(O—T)CH(R}^1\text{)COO—M} \qquad IV$$

wherein M is an alkali metal of alkaline earth metal, in optional sequence with an arylmethyl halide and a base g) selectively cleaving the resulting ether of the formula ti  $R^2$—CH(OCH—Ar)CH$_2$CH(O—T)CH(R$^1$)C-
OO—M tm V with an acid, h) cyclizing the resulting β-hydroxyacid of the formula $$R^2\text{—CH(OCH—Ar)CH}_2\text{CHOHCH(R}^1\text{)COOH} \qquad VI$$

optionally after resolution into its enantiomers, i) cleaving the resulting β-lactone ether of the formula

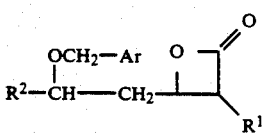

to give the compound of formula I, wherein X is hydrogen, and j) esterifying the resulting compound of formula I wherein X is hydrogen with an agent which introduces the group X', to give the compound of formula I'.

4. A process according to claim 3, wherein R$^1$ was n-hexyl and R$^2$ was undecyl.

5. A process for producing a compound having the formula:

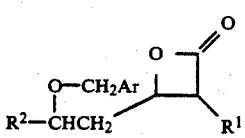

wherein R$^1$ and R$^2$ each, independently, is alkyl with up to 17 C atoms optionally interrupted by an O atom in a position other than the α- or β-position, or benzyl optionally ring-substituted by 1 to 3 C$_{1-6}$-alkyl or C$_{1-6}$-alkoxy groups; Ar is phenyl substituted by 1 to 3 R$^9$ or OR$^9$ groups wherein R$^9$ is hydrogen or C$_{1-3}$-alkyl; which process comprises the steps of:

(a) reacting a compound of the formula:

$$R^2\text{—CHOHCH}_2\text{CHO(O—T)CH(R}^1\text{)COO—M} \qquad IV$$

wherein T is a readily cleavable ether group and M is an alkali metal or alkaline earth metal, in optional sequence with an arylmethyl halide and a base; and (b) selectively cleaving the resulting diether of the formula:

$$R^2\text{—CH(OCH}_2\text{-Ar)CH}_2\text{CH(O—T)CH(R}^1\text{)C-}$$
$$\text{OO—M} \qquad V$$

with an acid, (c) cyclizing the resulting β-hydroxyacid of the formula:

$$R^2\text{—CH(OCH}_2\text{—Ar)CH}_2\text{CHOHCH(R}^1\text{)COOH} \qquad VI$$

optionally after resolution into its enantiomers, to form the compound of formula VII.

6. A process according to claim 5 wherein R$^1$ is n-hexyl and R$^2$ is undecyl.

7. A process according to claim 6 for producing (3S,4S)-3-hexyl-4-[(R)-2-benzyloxytridecyl ]-2-hexyl-2-oxetanone which comprises the steps of:

(a) reacting the sodium salt of (2RS,3RS,5SR)-2-hexyl-5-hydroxy-3-(tetrahydro-2H-pyran-2-yloxy) hexadecanoic acid with benzyl bromide and sodium hydride in THF;

(b) selectively cleaving the resulting sodium salt of (2RS,3RS,5SR)-2-hexyl-5-benzyloxy-3-(tetrahydro-2H-pyran-2-yloxy) hexadecanoic acid with hydrochloric acid;

(c) resolving into its enantiomers, the resulting rac-(2RS,3RS, 5SR)-5-benzyloxy-2-hexyl-3-hydroxyhexadecanoic acid; and (d) cyclizing the isolated (2S,3S,5R)-5-benzyloxy-2-hexyl-3-hydroxyhexadecanoic acid with benzenesulphonyl chloride to form (3S,4S)-4-[(R)-2-benzyloxytridecyl]-3-hexyl-2-oxetanone.

8. A process according to claim 1, wherein the compound of the formula $$R^2\text{—CH(OCH}_2\text{—Ar)CH}_2\text{CHOHCH(R}^1\text{)COOH} \qquad VI$$

is resolved into its enantiomers prior to being cyclized.

9. A process according to claim 8, wherein the compound of the formula

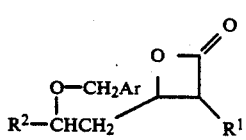

is cleaved by hydrogenation to form a compound of formula I wherein X is hydrogen, the resulting compound of formula I is purified and isolated by crystallization.

* * * * *